United States Patent

Tritsch

[11] 4,014,339
[45] Mar. 29, 1977

[54] DIAPER WITH COLLAPSIBLE ADHESIVE TAB FASTENER

[75] Inventor: Ludwig Tritsch, Wilmette, Ill.

[73] Assignee: Johnson & Johnson, New Brunswick, N.J.

[22] Filed: Mar. 12, 1976

[21] Appl. No.: 666,274

[52] U.S. Cl. .............................. 128/287; 128/284
[51] Int. Cl.$^2$ ......................... A61F 13/16
[58] Field of Search ...... 128/287, 284, 286, 290 R; 24/67 AR

[56] References Cited
UNITED STATES PATENTS

| | | | |
|---|---|---|---|
| 3,776,234 | 12/1973 | Hoey | 128/287 |
| 3,810,472 | 5/1974 | Aldinger et al. | 128/287 |
| 3,848,594 | 11/1974 | Buell | 128/284 |
| 3,930,502 | 1/1976 | Tritsch | 128/287 |
| 3,951,149 | 4/1976 | Ness et al. | 128/287 |

Primary Examiner—Stephen C. Pellegrino

[57] ABSTRACT

A disposable diaper having a facing sheet defining a diaper inside surface for direction toward an infant and a backing sheet defining a diaper outside surface is provided with adhesive tabs comprising an integral elongated tape ribbon which is folded to form a plurality of articulated segments. The tab forms a loop having inner and outer faces with a backing-anchoring segment and facing-anchoring segment at opposite ends of the tab. The anchoring segments are attached to the backing sheet and facing sheet, respectively, to distribute stresses which are imposed on the tab. A securing segment having pressure-sensitive adhesive means on the outer face thereof, and a release-bearing segment having release means on the outer face thereof, are positioned intermediate the anchoring segments. The adhesive means is contiguous to and protected by the release means when the tab is in a storage position, and can be separated therefrom when the tab is extended to a working position in which the adhesive means is available for securing the diaper about an infant. In one embodiment, further adhesive means and release means are provided to enable the diaper to be removed from the infant and thereafter refastened thereon by employing the further adhesive means.

10 Claims, 12 Drawing Figures

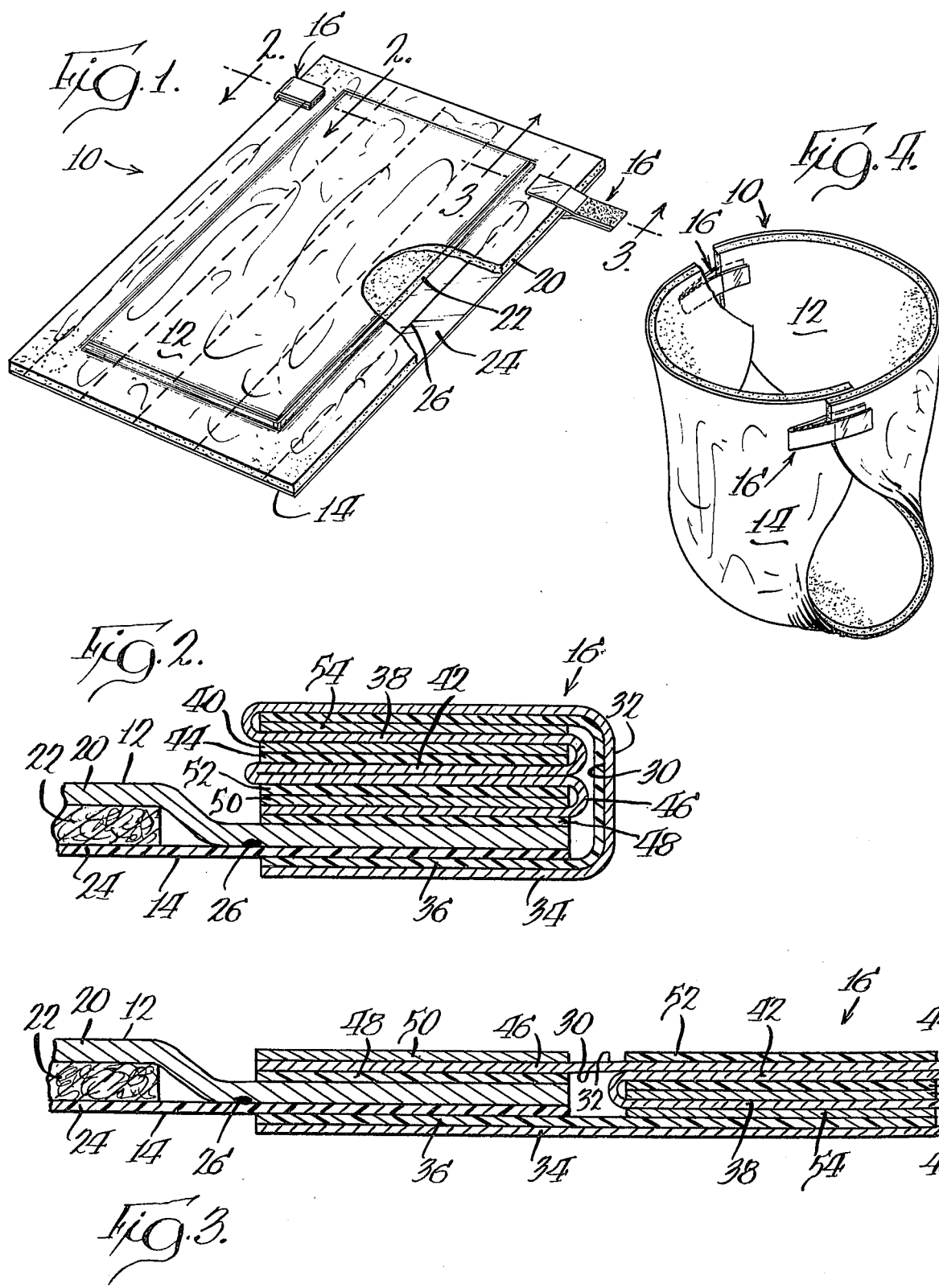

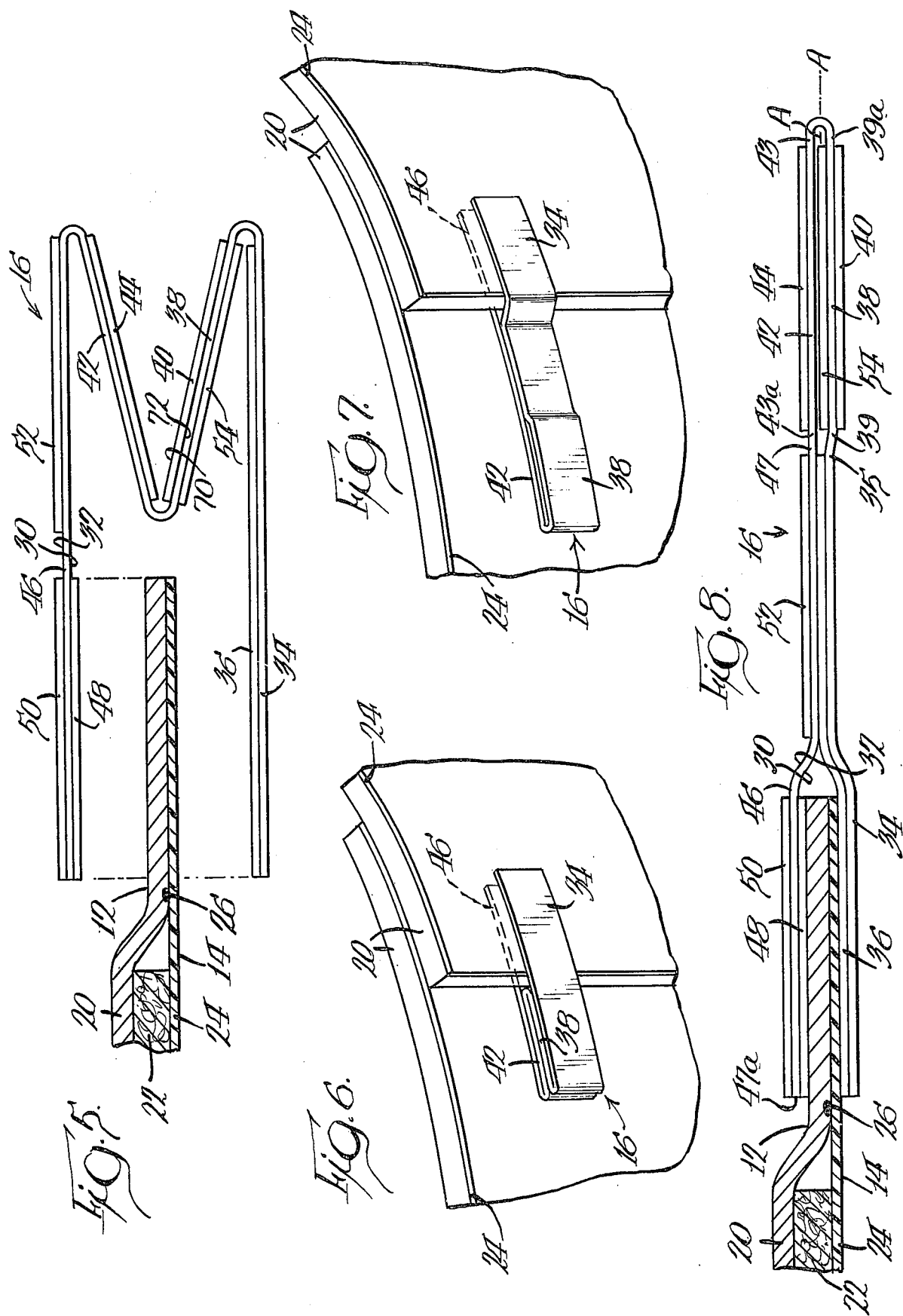

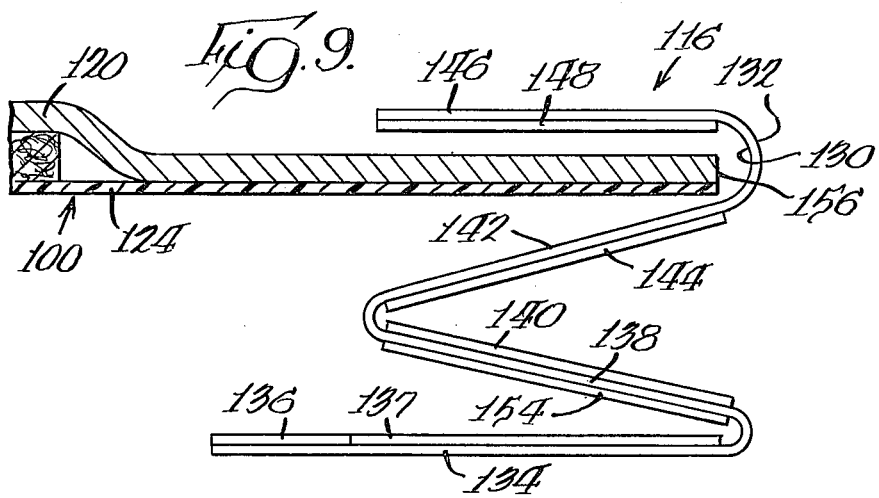
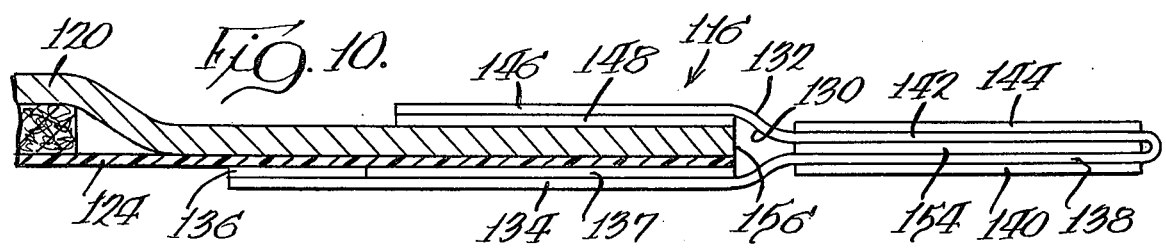
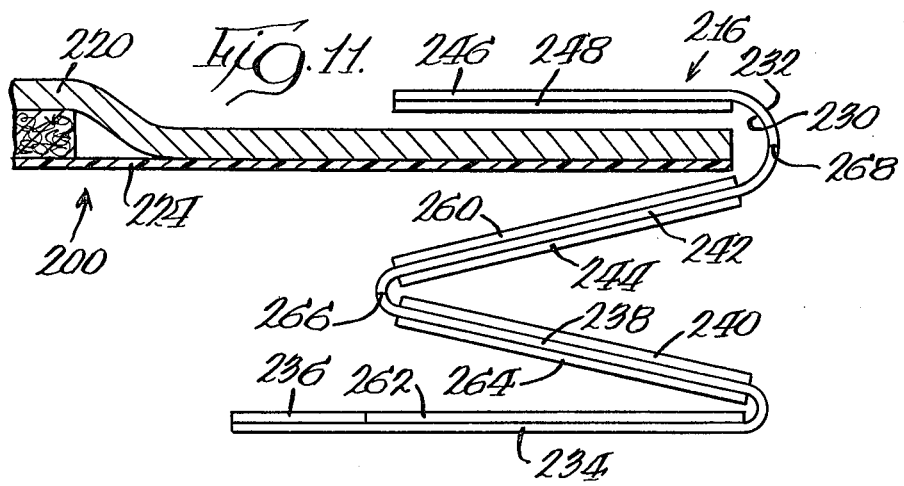
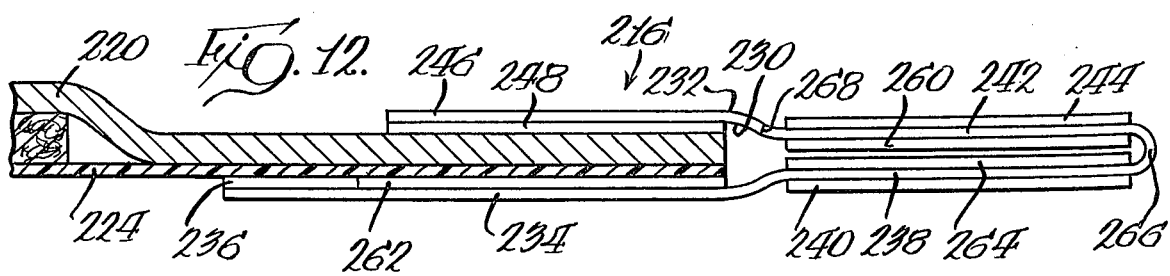

DIAPER WITH COLLAPSIBLE ADHESIVE TAB FASTENER

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re.26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces fro subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,646,937 to Gellert teaches a fastening tab which is provided with a release surface permanently bonded primarily to the inside surface of the diaper. One of the drawbacks of the Gellert arrangement is that in use the adhesive tape fasteners are permanently attached to only one surface of the diaper, generally the outside surface of the backing sheet, and thus the bond between one end of the tape fastener and the diaper backing sheet is subjected to all of the stresses exerted on the tape fastener during securement or as the infant moves about.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabric, may tear the facing fabric upon separation therefrom.

U.S. Pat. No. 3,776,234 to Hoey proposes to fold the tab over on itself at the diaper's edge and to adhesively attach a portion of the folded-over tab segment to an inwardly folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two co-extensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper. Such a construction takes away from the adhesive area that is available on the free tab end for diaper securement. It also has the disadvantage in that each tape fastener is comprised of two or more separate tape segments which are joined together so as to produce a common area of joinder for both fastener anchoring legs and the fastener securing portions, thereby adding complexities and expense to the manufacturing process, as well as requiring careful positioning during diaper manufacture.

SUMMARY OF THE INVENTION

A single integral elongated tape tab segment comprising a tape ribbon is used on each side of a disposable diaper to secure the diaper about an infant. The diaper has a facing sheet defining a diaper inside surface for direction toward an infant and a backing sheet defining a diaper outside surface.

According to the present invention, each tab is folded to form a plurality of articulated segments each having an inner face and an outer face. A backing-anchoring segment and a facing-anchoring segment are provided at opposite ends of the tab, receive a marginal portion of the diaper therebetween, and are permanently attached to the backing sheet and facing sheet, respectively, to distribute stresses which are imposed on the tab. A securing segment having first pressure-sensitive adhesive means on the outer face thereof, and a release-bearing segment having release means on the outer face thereof, are connected at one end to each other and are positioned intermediate the anchoring segments or legs. The securing segment has an opposite end connected to the facing-anchoring segment, and the release-bearing segment has an opposite end connected to the backing-anchoring segment.

The tab is movable from a position in which the first adhesive means is contiguous to and protected by the release means, to a fully extended working position in which the first adhesive means is completely separated from the release means and is available for securing the diaper about an infant.

If desired, auxiliary release means can be provided at the distal end of the facing-anchoring segment on the outer face thereof, and second pressure-sensitive adhesive means on the remaining portion of the outer face of the facing-anchoring segment. The tab is movable from a storage position, in which the first and second pressure-sensitive adhesive means are contiguous to and protected by the release means and the auxiliary release means, respectively, to an intermediate working position in which the inner face of the securing segment is juxtaposed to the inner face of the facing-anchoring segment, the first adhesive means remains contiguous to the release means, and the second adhesive means is available for securing the diaper about the infant. In addition, the tab is movable to a fully extended working position in which the inner face of the release-bearing segment is juxtaposed to the inner face of the securing segment and the first and second adhesive means both are available for securing the diaper about the infant.

In another embodiment, first pressure-sensitive adhesive means is provided on the outer face of the securing segment and is releasably attached to release means on the outer face of the release-bearing segment when the tab is in a storage position. Third pressure-sensitive adhesive means is provided on the inner face of the release-bearing segment, and further auxiliary release means, coextensive with the third adhesive means, are provided on the inner face of the securing segment and on a portion of the inner face of the backing-anchoring segment. The third adhesive means is releasably attached to the auxiliary release means on the backing-anchoring segment when the tab is in a storage position, and is releasably attached to the auxiliary release means on the securing segment when the tab is in a fully extended working position in which the first adhesive means is available for securing the tab about an infant. The applied diaper can be opened for inspection or adjustment by severing the tab on opposite sides of the securing segment. The diaper can thereafter be refastened on the infant by employing the third adhesive means.

The tape tab fasteners of the present invention remain flat against the diaper when in the folded configuration and will not interfere with the diaper maufacturing machinery and the subsequent folding and packaging operations. Additional features of this invention include the utilization of an integral tape tab which is relatively easy to affix to the diaper and provides good bond strength, and permanent attachment of the tab to both the diaper facing sheet and backing sheet, so that when stress is imposed on the tab of an applied diaper, the stress is distributed between the facing sheet and the backing sheet, thereby reducing the possibility of undesirable rupture of the backing sheet. In addition, the tape tab fastener in accordance with one of the embodiments of this invention provides secondary fastening means which permits the diaper to be opened or completely removed from an infant and thereafter refastened or reapplied thereto.

BRIEF DESCRIPTION OF THE DRAWINGS

FIG. 1 is a perspective view, partially broken away to show interior detail, of an open unfolded diaper in accordance with one of the embodiments of the invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3;

FIG. 4 is a perspective view of the diaper of FIG. 1 in a configuration assumed by the diaper when placed about an infant;

FIG. 5 is an exploded fragmentary cross-sectional view similar to FIG. 3;

FIG. 6 is a fragmentary perspective view illustrating the tab fastener of this invention as applied in an intermediate position;

FIG. 7 is a fragmentary perspective view, similar to FIG. 6, illustrating the tab fastener of this invention as applied in a fully extended working position;

FIG. 8 is a fragmentary cross-sectional view illustrating the tab fastener of this invention as applied in a fully extended working position;

FIG. 9 is an exploded fragmentary cross-sectional view of an alternate embodiment of the invention in a partially folded storage position;

FIG. 10 is a fragmentary cross-sectional view illustrating the embodiment of FIG. 9 in an extended working position;

FIG. 11 is an exploded fragmentary cross-sectional view illustrating another embodiment of the invention in a partially folded-over storage position; and FIG. 12 is a fragmentary cross-sectional view illustrating the embodiment of FIG. 11 in the extended working position.

DESCRIPTION OF THE PREFERRED EMBODIMENTS

In the following description, two digit numerals are used to refer to the embodiment illustrated in FIGS. 1–8, three digit numerals in the one hundred series are used to refer to the embodiment illustrated in FIGS. 9 and 10, and three digit numerals in the two hundred series are used to refer to the embodiment illustrated in FIGS. 11 and 12. The same last two digits in each numeral designate similar elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to an intermediate position which is illustrated in FIG. 3, and to a fully extended working position shown in FIG. 8.

Referring to FIGS. 1–8, diaper 10 comprises moisture-pervious facing sheet 20 which defines diaper inside surface 12, overlying a moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made coextensive with backing sheet 24, if desired. Facing sheet 20 is substantially coextensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2, 3, 5 and 8, adhesive tab 16 comprises an integral elongated tape ribbon which is folded to form a plurality of articulated segments. As shown in FIG. 8, tab 16 is folded over about a first fold line A—A to form a loop having an inner face 30 and an outer face 32. The articulated segments of tab 16 include a backing-anchoring segment 34 at one end of the tab which has adhesive means 36 on at least a portion of the inner face 30 thereof to secure the backing-anchoring segment 34 to backing sheet 24. Release-bearing segment 38 is connected at one end 39 to an adjacent end 35 of backing-anchoring segment 34 and has an opposite end 39a. Release means 40 is provided on outer face 32 of release-bearing segment 38. Securing segment 42, having a first pressure-sensitive adhesive means 44 on outer face 32 thereof, is connected at one end 43 to opposite end 39a of release-bearing segment 38 and has opposite end 43a. Facing-anchoring segment 46 is provided at the opposite end of tab 16 and is connected at one end 47 to opposite end 43a of securing segment 42 and has an opposite distal end 47a. Facing adhesive means 48 is provided on at least a portion of inner face 30 of facing-anchoring segment 46 to secure the facing-anchoring segment to facing sheet 20. Tab 16 receives a marginal portion of diaper 10 between backing-anchoring segment 34 and facing-anchoring segment 46, and the anchoring segments 34 and 46 are permanently attached to backing sheet 20 and facing sheet 24 by means of adhesive means 36 and 48, respectively, so that stresses exerted on tab 16 are distributed to both surfaces of the diaper. Adhesive means 36 and 48 comprise adhesive coatings which can be made of a pressure-sensitive adhesive composition, a heat-activated or solvent-activated adhesive composition, or the like.

Tab 16 is further folded during manufacture to the intermediate position depicted in FIG. 3 in which release means 40 is contiguous to and protects first pressure-sensitive adhesive means 44 on outer face 32 of securing segment 42.

In the embodiment illustrated in FIGS. 1-8, anchoring segments 34 and 46 preferably are of substantially equal length and are longer than release-bearing segment 38 and securing segment 42. Auxiliary release means 50 is provided at the distal end of facing-anchoring segment 46 on outer face 32 thereof, and a second pressure-sensitive adhesive means 52 is provided on outer face 32 of facing-anchoring segment 46 between auxiliary release means 50 and securing segment 42. Tab 16 is thereby arranged in the storage position illustrated in FIG. 2 wherein auxiliary release means 50 is contiguous to second pressure-sensitive adhesive means 52. Tab 16 can be moved to the intermediate position depicted in FIGS. 3 and 6 and which comprises a first working position wherein inner face 30 of securing segment 42 is juxtaposed to inner face 30 of facing-anchoring segment 46 and second pressure-sensitive adhesive means 52 is aviailable for securing diaper 10 about an infant. Tab 16 can be further unfolded to the fully extended second working position shown in FIGS. 7 and 8 in which inner face 30 of release-bearing segment 38 is juxtaposed to inner face 30 of securing segment 42 and both adhesive means 44 on securing segment 42 and second pressure-sensitive adhesive means 52 on facing-anchoring segment 46 are available for securing diaper 10 about an infant.

Adhesive means such as coating 36 on backing-anchoring segment 34 may be pressure-sensitive and substantially coextensive with inner face 30 of backing-anchoring segment 34, in which case another auxiliary release means 54 is provided on inner face 30 of release-bearing segment 38 for releasable attachment in the storage and intermediate positions to that portion of adhesive coating 36 which is not secured to backing sheet 24. When tab 16 is in the extended second working position shown in FIG. 8, the portion of adhesive coating 36 which is not secured to backing sheet 24 is attached to a corresponding portion of facing-anchoring segment 46 which is not attached to facing sheet 20 to facilitate the distribution of stresses imposed on tab 16 to both facing sheet 20 and backing sheet 24 and to minimize the possibility of undesirable rupture or undue extension thereof.

If desired, first pressure-sensitive adhesive means 44 on securing segment 42 and second pressure-sensitive adhesive means 52 on facing-anchoring segment 46 may together comprise a substantially continuous adhesive coating.

In the embodiment illustrated in FIGS. 9 and 10, release-bearing segment 138, securing segment 142 and facing-anchoring segment 146 are substantially equal in length, and backing-anchoring segment 134 is longer than facing-anchoring segment 146. Adhesive means such as pressure-sensitive adhesive coating 148 on inner face 130 of facing-anchoring segment 146 covers substantially the entire inner face 130 of facing-anchoring segment 146 and is adhesively attached to facing sheet 120. Backing-anchoring segment 134 is adhesively attached to backing sheet 124 by means of adhesive means such as pressure-sensitive adhesive coating 136 on the inner face 130 of the distal end thereof. A portion of the longitudinal margin of diaper 100 is received between inner face 130 of securing segment 142 and inner face 130 of facing-anchoring segment 146 when tab 116 is in the storage position which is shown in an exploded view in FIG. 9. Tab 116 is folded about longitudinal edge 156 of diaper 100 when tab 116 is in the storage position so that longitudinal edge 156 is positioned between facing-anchoring segment 146 and securing segment 142, and adhesive coating 144 on outer face 132 of securing segment 142 is releasably attached to release means such as release coating 140 on outer face 132 of release-bearing segment 138. Tab 116 is movable to the extended working position illustrated in FIG. 10 in which adhesive coating 144 is available for securing the diaper about an infant and is adjacent to longitudinal edge 156.

If desired, adhesive coating 137 may be provided on the remaining portion of inner face 130 of backing-anchoring segment 134, and adhesive means 136 and 137 may together comprise a continuous coating of adhesive on backing-anchoring segment 134. Auxiliary release means such as release coating 154 is provided on inner face 130 of release-bearing segment 138 for releasable attachment to adhesive means 137 when tab 116 is in the storage position. Adhesive coating 137 is adapted for adhesive attachment to backing sheet 124 when tab 116 is in the working position.

Referring to FIGS. 11 and 12, diaper 200 has tab 216 with facing-anchoring segment 246 attached to facing sheet 220 by means of adhesive means 248, and backing-anchoring segment 234 is attached to backing sheet 224 by means of adhesive means 236. Release-bearing segment 238 and securing segment 242 are of substantially equal length and are positioned between anchoring segments 234 and 246. Third auxiliary release means 260 is provided on inner face 230 of securing segment 242 and fourth auxiliary release means 262 is provided on a portion of inner face 230 of backing-anchoring segment 234. First pressure-sensitive adhesive means 244 is provided on outer face 232 of securing segment 242, and third pressure-sensitive adhesive means 264 is provided on inner face 230 of release-bearing segment 238. Transverse lines of weakening 266 and 268 are provided at the juncture of release-bearing segment 238 and securing segment 242 and at the juncture of securing segment 242 and facing-anchoring segment 246, to enable a user to unfasten tab 216 to remove diaper 200 from an infant.

Third and fourth auxiliary release means 260 and 262 are both substantially coextensive with third pressure-sensitive adhesive means 264. When tab 216 is in the storage position shown in an exploded view in FIG. 11, first pressure-sensitive adhesive means 244 is releasably attached to release means 240 on outer face 232 of release-bearing segment 238, and third pressure-sensitive adhesive means 264 is releasably attached to fourth auxiliary release means 262. Third pressure-sensitive adhesive means 264 is releasably attached to third auxiliary release means 260 when tab 216 is in the extended working position shown in FIG. 12 in which first pressure-sensitive adhesive means 244 is available for securing the diaper about an infant. If a user desires to inspect the diaper for wetting or to reposition the diaper, the user can sever tab 216 along transverse lines of weakening 266 and 268 and separate third pressure-sensitive adhesive means 264 from its releasable attachment to third auxiliary release means 260. The user can thereafter refasten diaper 200 about the infant by employing third pressure-sensitive adhesive means 264 as desired.

Referring now to all of the embodiments discussed hereinabove, the release means and auxiliary release means may comprise ribbon segments or release strips such as segments or strips 40 provided with release coated face 70 (FIG. 5) which provides the release region, and an adhesive coating on opposite face 72 by means fo which release strip 40 is anchored to the tape ribbon. Alternatively, the release means may comprise a release coating, such as a silicone release compound, or the like printed onto release-bearing segment 38 and substantially coextensive with adhesive means 44 on securing segment 42 when tab 16 is in the storage position.

Adhesive tabs suitable for the purposes of the present invention can be made from a wide variety of materials, provided that such materials are sufficiently flexible. Preferred materials for this purpose are polyolefin webs such as polyethylene sheet, polypropylene sheet, and the like. Particularly preferred are webs which are oriented along the narrow dimension of the tab or webs which have filament reinforcements therein.

The pressure-sensitive adhesive means such as adhesive coating 44 are provided by applying a coating of a pressure-sensitive adhesive composition known in the art to the appropriate surface portion of tab 16. The applied adhesive shall have good tack, good cohesive stength, good resistance to moisture and good resistance to aging. Illustrative of such adhesive compositions are mixtures of natural or synthetic rubber, zinc oxide, and various resins, also latices of natural or synthetic rubber, or water dispersions of tacky acrylic polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or coton linters, in amounts of about 75 to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry stength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous non-woven tarting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 20 can be formed of a non-apertured material, such as a non-woven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling adhesive-coated securing segment 42 away from its temporary engagement with release means 40 and extending tab 16 to the working position, whereupon tabs 16 are used to secure the diaper in the desired position by simply urging the pressure-sensitive adhesive means 44 in contact with the adjacent outer surface of the diaper. The applied diaper assumes the configuration illustrated in FIG. 4.

The foregoing description and the drawings are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet subbstantially coextensive with said facing sheet and defining a diaper outside surface, an absorbent panel positioned between said facing sheet and said backing sheet, and an adhesive tab fastener means which comprises:
   an integral tape ribbon folded to form a plurality of articulated segments including a backing-anchoring segment which is secured to said backing sheet, a release-bearing segment connected at one end to an adjacent end of said backing-anchoring segment and having an opposite end, a securing segment connected at one end to said opposite end of said release-bearing segment and having an opposite end, and a facing-anchoring segment connected at one end to said opposite end of said securing segment and having an opposite distal end which is secured to said facing sheet, each segment having an inner face and an outer face;
   a first pressure-sensitive adhesive means on the outer face of said securing segment; and
   release means on the outer face of said release-bearing segment contiguous to and protecting said first pressure-sensitive adhesive means when the tab fastener is in a storage position, said first pressure-sensitive adhesive means being removable from said release means to assume a working position wherein said first pressure-sensitive adhesive means is available for securing the diaper about an infant.

2. The disposable diaper as defined in claim 1 wherein:
   pressure-sensitive backing adhesive means is provided and is coextensive with the inner face of said backing-anchoring segment for securing said backing-anchoring segment to said backing sheet,
   pressure-sensitive facing adhesive means on at least a portion of the inner face of said facing-anchoring segment for securing said facing-anchoring segment to said facing sheet, and
   first auxiliary release means is provided on the inner face of said release-bearing segment for releasable attachment to that portion of said backing adhesive means which is not secured to the backing sheet.

3. The disposable diaper as defined in claim 2 wherein: said anchoring segments are of substantially equal length and are longer than said release-bearing segment and said securing segment; second auxiliary release means is provided at the distal end of the facing-anchoring segment on the outer face thereof; and second pressure-sensitive adhesive means is provided on the outer face of said facing-anchoring segment between said second auxiliary release means and said securing segment;
   said second auxiliary release means being contiguous to said second pressure-sensitive adhesive means when the tab fastener is in a storage position; and
   the inner face of said securing segment being juxtaposed to the inner face of said facing-anchoring segment when the tab fastener is in a first working position, and the inner face of said release-bearing segment being juxtaposed to the inner face of said securing segment when the tab fastener is in a second working position.

4. The disposable diaper as defined in claim 3 wherein said first and second pressure-sensitive adhesive means on said securing segment and on said facing-anchoring segment, respectively, together comprise a substantially continuous adhesive coating.

5. The disposable diaper as defined in claim 3 wherein said facing adhesive means is pressure-sensitive.

6. The disposable diaper as defined in claim 1 wherein said release-bearing segment, said securing segment, and said facing-anchoring segment are substantially equal in length; wherein said backing-anchoring segment is longer than said facing-anchoring segment; wherein facing adhesive means is provided on substantially the entire inner face of said facing-anchoring segment and is adhesively attached to said facing sheet; and wherein a portion of the longitudinal margin of said diaper is received between the inner faces of said securing segment and said facing-anchoring segment when the tab fastener is in a storage position.

7. The disposable diaper as defined in claim 6 wherein pressure-sensitive backing adhesive means is provided and is substantially coextensive with the inner face of said backing-anchoring segment for securing said backing-anchoring segment to said backing sheet; and wherein an auxiliary release means is provided on the inner face of said release-bearing segment for releasable attachment to that portion of said backing adhesive means which is not secured to the backing sheet when the tab fastener is in a storage position;

said portion of the backing adhesive means releasably attached to said first auxiliary release means being adapted for adhesive attachment to said backing sheet when the tab fastener is in a working position.

8. The disposable diaper as defined in claim 7 wherein said facing adhesive means is pressure-sensitive.

9. The disposable diaper as defined in claim 1 wherein said release-bearing segment and said securing segment are of substantially equal length; wherein the inner face of said securing segment and a portion of the inner face of said backing-anchoring segment adjacent to the inner face of said release-bearing segment are provided respectively with third and fourth auxiliary release means; wherein third pressure-sensitive adhesive means is provided on the inner face of said release-bearing segment; and wherein transverse lines of weakening are provided at the juncture of said release-bearing segment and said securing segment and at the juncture of said securing segment and said facing-anchoring segment;

said third and fourth auxiliary release means being substantially coextensive with said third pressure-sensitive adhesive means, said third pressure-sensitive adhesive means being releasably attached to said fourth auxiliary release means when the tab fastener is in a storage position and releasably attached to said third auxiliary release means when the tab fastener is in said working position, and said tab fastener being severable along said transverse lines of weakening to remove said diaper from said infant, whereupon said third pressure-sensitive adhesive means may be employed to refasten said diaper about said infant.

10. The disposable diaper as defined in claim 9 wherein pressure-sensitive backing adhesive means is provided on the inner face of said backing-anchoring segment for securing said backing-anchoring segment to said backing sheet, and wherein pressure-sensitive facing adhesive means is provided on the inner face of said facing-anchoring segment for securing said facing-anchoring segment to said facing sheet.

* * * * *